US008920322B2

(12) United States Patent
Mansi et al.

(10) Patent No.: US 8,920,322 B2
(45) Date of Patent: Dec. 30, 2014

(54) VALVE TREATMENT SIMULATION FROM MEDICAL DIAGNOSTIC IMAGING DATA

(75) Inventors: Tommaso Mansi, Westfield, NJ (US); Ingmar Voigt, Erlangen (DE); Razvan Ioan Ionasec, Lawrenceville, NJ (US); Bogdan Georgescu, Plainsboro, NJ (US); Dorin Comaniciu, Princeton Junction, NJ (US); Etienne Assoumou Mengue, Highland Park, NJ (US)

(73) Assignee: Siemens Aktiengesellschaft, Munich (DE)

( * ) Notice: Subject to any disclaimer, the term of this patent is extended or adjusted under 35 U.S.C. 154(b) by 1 day.

(21) Appl. No.: 13/411,711

(22) Filed: Mar. 5, 2012

(65) Prior Publication Data

US 2012/0232386 A1 Sep. 13, 2012

Related U.S. Application Data

(60) Provisional application No. 61/450,850, filed on Mar. 9, 2011.

(51) Int. Cl.
*A61B 8/00* (2006.01)
*A61B 8/08* (2006.01)
*A61B 19/00* (2006.01)
*G06T 19/00* (2011.01)
*A61B 6/00* (2006.01)
*A61F 2/24* (2006.01)
*G06F 19/00* (2011.01)

(52) U.S. Cl.
CPC ............ *A61B 8/5238* (2013.01); *A61B 8/0883* (2013.01); *A61B 19/50* (2013.01); *G06T 19/00* (2013.01); *A61B 6/503* (2013.01); *A61B 6/5229* (2013.01); *A61F 2/24* (2013.01); *G06F 19/3437* (2013.01); *G06T 2210/41* (2013.01); *A61B 2019/504* (2013.01)
USPC ............ 600/437; 600/407; 600/425; 600/439

(58) Field of Classification Search
USPC .......... 600/407, 410, 424, 425, 427, 437, 439
See application file for complete search history.

(56) References Cited

U.S. PATENT DOCUMENTS 7,702,596 B2  4/2010  Tu et al.
7,916,919 B2  3/2011  Zheng et al.

(Continued)

OTHER PUBLICATIONS

Allard, J. et al., "Sofa—an open source framework for medical simulation," Medicine Meets Virtual Reality, MMVR 15, pp. 1-6, (2007).

(Continued)

*Primary Examiner* — Peter Luong

(57) ABSTRACT

Valve treatment simulation is performed from patient specific imaging data for therapy planning. A model of the valve may be generated from the patient specific data automatically or with very minimal user indication of anatomy locations relative to an image. Any characteristics for the valve not extracted from images of the patient may be added to create a volumetric model. Added characteristics include chordae, such as chordae length and leaflet fiber direction. The characteristics may be adjusted based on user feedback and/or comparison with images of the patient. The effect of therapy on closure of the valve may be simulated from the model. For instance, mitral clip intervention is simulated on the patient-specific model. Valves are deformed according to the clip location. Valve closure is then simulated to predict effect of the therapy in terms of mitral regurgitation.

18 Claims, 6 Drawing Sheets

(56) References Cited

U.S. PATENT DOCUMENTS

| | | | |
|---|---|---|---|
| 8,009,887 | B2 | 8/2011 | Ionasec et al. |
| 8,311,791 | B1* | 11/2012 | Avisar .............................. 703/11 |
| 2004/0153128 | A1* | 8/2004 | Suresh et al. ................... 607/14 |
| 2009/0123050 | A1 | 5/2009 | Ionasec et al. |
| 2010/0070249 | A1 | 3/2010 | Ionasec et al. |
| 2010/0240996 | A1 | 9/2010 | Ionasec et al. |
| 2010/0280352 | A1 | 11/2010 | Ionasec et al. |
| 2011/0153286 | A1 | 6/2011 | Zaeuner et al. |
| 2011/0191283 | A1 | 8/2011 | Voigt et al. |

OTHER PUBLICATIONS

Arcaro, V., "A simple procedure for shape finding and analysis of fabric structures," Abstract, pp. 1-16, 2006.

Avanzini, A., "A computational procedure for prediction of structural effects of edge-to-edge repair on mitral valve," Journal of biomechanical engineering, vol. 130, pp. 031015-1-031015-10, 2008.

Avanzini, A. et al., "Functional and structural effects of percutaneous edge-to-edge double-orifice repair under cardiac cycle in comparison with suture repair," Proceedings of the Institution of Mechanical Engineers, Part H: Journal of Engineering in Medicine 225, pp. 959-971, 2011.

Baraff, D. et al., "Large steps in cloth simulation," In: Proceedings of the 25th Annual Conference on Computer Graphics and Interactive Techniques, ACM, pp. 43-54, 1998.

Burlina, P. et al., "Patient-specific modeling and analysis of the mitral valve using 3d-tee," Information Processing in Computer-Assisted Interventions, pp. 135-146, 2010.

Chandra, S. et al., "A three-dimensional insight into the complexity of flow convergence in mitral regurgitation: adjunctive benefit of anatomic regurgitant orifice area," American Journal of Physiology—Heart and Circulatory Physiology 301, pp. H1015-H1024, 2011.

Conti, C. et al., "Mitral valve modeling in ischemic patients: Finite element analysis from cardiac magnetic resonance imaging," In: Computers in Cardiology, IEEE, pp. 1059-1062, 2010.

Einstein, D. et al., "Fluid-structure interactions of the mitral valve and left heart: Comprehensive strategies, past, present and future." International Journal for Numerical Methods in Biomedical Engineering 26, pp. 348-380, 2010.

Feldman, T. et al., "Percutaneous mitral repair with the mitraclip system: Safety and midterm durability in the initial everest (endovascular valve edge-to-edge repair study) cohort," Journal of the American College of Cardiology 54, pp. 686-694, 2009.

Grashow, J. et al., "Biaixal stress-sketch behavior of the mitral valve anterior leaflet at physiologic strain rates," Annals of biomedical engineering 34, pp. 315-325, 2006.

Grbić, S. et al., "Complete valvular heart apparatus model from 4d cardiac ct," In: Medical Image Computing and Computer-Assisted Intervention—MICCAI, Springer, pp. 218-226, 2010.

Hammer, P. et al., "Anisotropic mass-spring method accurately simulates mitral valve closure from image-based models," In: Functional Imaging and Modeling of the Heart, Springer, pp. 233-240, 2011.

Hammer, P. et al., "Fast image-based model of mitral valve closure for surgical planning," In: Computational Biomechanics for Medicine (MICCAI'08 Workshop), pp. 15-26, 2008.

Herrmann, H. et al., "Percutaneous mitral valve edge-to-edge repair with the evalve mitraclip system: rationale and phase i results," EuroIntervention 1, pp. A36-A39, 2006.

Ionasec, R. et al., "Patient-Specific Modeling and Quantification of the Aortic and Mitral Valves from 4-D Cardiac CT and TEE," Medical Imaging, IEEE Transactions on 29, pp. 1636-1651, 2010.

Iung, B. et al., "Epidemiology of valvular heart disease in the adult," Nature Reviews Cardiology 8, pp. 162-172, 2011.

Jassar, A. et al., "Quantitative mitral valve modeling using real-time three-dimensional echocardiography: Technique and repeatability," The Annals of thoracic surgery 91, pp. 165-171, 2011.

Krishnamurthy, G. et al., "Stress-strain behavior of mitral valve leaflets in the beating ovine heart," Journal of biomechanics 42, pp. 1909-1916, 2009.

Kunzelman, K. et al., "Mechanical properties of basal and marginal mitral valve chordae tendineae," ASAIO Journal 36, pp. M405-M408, 1990.

Zheng, Y. et al., "Four-chamber heart modeling and automatic segmentation for 3-d cardiac ct volumes using marginal space learning and steerable features," Medical Imaging, IEEE Transactions on 27, pp. 1668-1681, 2008.

Kunzelman, K. et al., "Fluid-structure interaction models of the mitral valve: function in normal and pathological states," Philosophical Transactions of the Royal Society B: Biological Sciences 362, pp. 1393-1406, 2007.

Lau, K. et al., "Mitral valve dynamics in structural and fluid-structure interaction models," Mechanical engineering & physics 32, pp. 1057-1064, 2010.

Lau, K. et al., "Fluid-structure interaction study of the edge-to-edge repair technique on the mitral valve," Journal of Biomechanics 44, pp. 2409-2417, 2011.

Maisano, F. et al., "The edge-to-edge technique: a simplified method to correct mitral insufficiency," European Journal of Cardiothoracic Surgery 13, p. 240-246, 1998.

Mansi, T. et al., "Towards Patient-Specific Finite-Element Simulation of MitralClip Procedure," In: Medical Image Computing and Computer-Assisted Intervention—MICCAI, Springer, pp. 452-459, 2011.

May-Newman, K. et al., "Biaxial mechanical behavior of excised porcine mitral valve leaflets," American Journal of Physiology—Heart and Circulatory Physiology 269, pp. H1319-H1327, 1995.

May-Newman, K. et al., "A constitutive law for mitral valve tissue," Journal of biomechanical engineering, vol. 120, pp. 38-47, 1998.

Nesme, M. et al., "Efficient, physically plausible finite elements," Eurographics (short papers), pp. 77-80, 2005.

Nkomo, V. et al., "Burden of valvular heart diseases: a population-based study," The Lancet, vol. 368, pp. 1005-1011, 2006.

Powell, M., "Developments of newuoa for minimization without derivatives," IMA journal of numerical analysis, vol. 28, pp. 649-664, 2008.

Prot, V. et al., "Finite element analysis of the mitral apparatus: annulus shape effect and chordal force distribution," Biomechanics and modeling in mechanobiology 8, pp. 43-55, 2009.

Prot, V. et al., "Transversely isotropic membrane shells with application to mitral valve mechanics, constitutive modeling and finite element implementation," International Journal for Numerical Methods in Engineering 71, pp. 987-1008, 2007.

Prot, V. et al., "On modeling and analysis of healthy and pathological human mitral valves: two case studies," Journal of the Mechanical Behavior of Biomedical Materials 3, pp. 167-177, 2010.

Sacks, M. et al., "On the biomechanics of heart valve function," Journal of biomechanics 42, pp. 1804-1824, 2009.

Schievano, S. et al., "Percutaneous mitral valve dilatation: Single balloon ver-sus double balloon, a finite element study," Journal of Heart Valve Disease 18, pp. 28-34, 2009.

Schneider, R. et al., "Modeling mitral valve leaflets from three-dimensional ultrasound," In: Functional Imaging and Modeling of the Heart—FIMH, Springer, pp. 215-222, 2011.

Schneider, R. et al., "Mitral annulus segmentation from four-dimensional ultrasound using a valve state predictor and constrained optical flow," Medical Image Analysis, 2011.

Schneider, R. et al., "Real-time image-based rigid registration of three-dimensional ultrasound," Medical Image Analysis, 2011.

Schneider, R. et al., "Patient-specific mitral leaflet segmentation from 4D ultrasound," In: Medical Image Computing and Computer-Assisted Intervention—MICCAI, Springer, pp. 520-527, 2011.

Skallerud, B. et al., "Modeling active muscle contraction in mitral valve leaflets during systole: a first approach," Biomechanics and Modeling in Mechanobiology 10, pp. 11-26, 2011.

Sprouse, C. et al., "Computational hemo-dynamic modeling based on transesophageal echocardiographic imaging," In: Engineering in Medicine and Biology Society, EMBC, Annual International Conference of the IEEE, IEEE, pp. 3649-3652, 2009.

(56) References Cited

OTHER PUBLICATIONS

Stevanella, M. et al., "Mitral leaflet modeling: Importance of in vivo shape and material properties," Journal of biomechanics 44, pp. 2229-2235, 2011.

Stevanella, M. et al., "Mitral valve patient-specific finite element modeling from cardiac mri: Application to an annuloplasty procedure," Cardiovascular Engineering and Technology, 1-1110.1007/s13239-010-0032-4, 2011.

Swanson, J. et al., "Electromechanical coupling between the atria and mitral valve," American Journal of Physiology—Heart and Circulatory Physiology 300, H1267-H1273, 2011.

Voigt, I. et al., "Robust physically-constrained modeling of the mitral valve and subvalvular apparatus," In: Medical Image Computing and Computer-Assisted Intervention—MICCAI, Springer, pp. 504-511, 2011.

Voigt, I. et al., "Patient-specific model of left heart anatomy, dynamics and hemodynamics from 4d tee: a first validation study," In: Functional Imaging and Modeling of the Heart—FIMH, Springer, pp. 341-349, 2011.

Votta, E. et al., "Mitral valve finite-element modeling from ultrasound data: a pilot study for a new approach to understand mitral function and clinical scenarios," Philosophical Transactions of the Royal Society A: Mathematical, Physical and Engineering Sciences 366, p. 3411-3434, 2008.

Votta, E. et al., "The geoform disease-specific annuloplasty system: a finite element study," The Annals of thoracic surgery 84, pp. 92-101, 2007.

Votta, E. et al., "3-d computational analysis of the stress distribution on the leaflets after edge-to-edge repair of mitral regurgitation," The Journal of heart valve disease 11, p. 810-822, 2002.

\* cited by examiner

VALVE TREATMENT SIMULATION FROM MEDICAL DIAGNOSTIC IMAGING DATA

RELATED APPLICATIONS

The present patent document claims the benefit of the filing dates under 35 U.S.C. §119(e) of Provisional U.S. Patent Application Ser. Nos. 61/450,850, filed Mar. 9, 2011, and 61/590,948, filed Jan. 26, 2012, which are hereby incorporated by reference.

BACKGROUND

The present embodiments relate to valve modeling. The mitral valve (MV), located between the left atrium (LA) and the left ventricle (LV), controls the unidirectional blood flow from the LA towards the LV. The MV is a complex cardiac structure including two leaflets, the mitral annulus and tendineae chordae. The leaflets are attached to the left heart through the fibrous mitral annulus, whereas the other extremity, called free-edge, is tethered to the papillary muscles through the tendineae chordae. During diastole, the leaflets open as the blood enters the LV. When the myocardium starts to contract, the leaflets close to prevent the blood from going back to the atrium. Tendineae chordae tighten to ensure closure.

Mitral valve disease is one of the most common heart valve diseases, with a prevalence increasing with age. In mitral valve disease, blood flows back towards the LA during systole, so-called mitral regurgitation, decreasing cardiac efficiency. In severe cases, a surgical intervention may be necessary to repair, or even replace the incompetent valve. Suturing the two mitral leaflets together at the regurgitant hole may help patients with severe mitral insufficiency due to leaflet prolapse or calcified annulus. In the percutaneous edge-to-edge technique, the leaflets are attached using a clip delivered through a catheter. For these or other forms of clipping, careful preoperative planning is necessary to select respondent patients and to determine the clipping sites. Strict guidelines, such as the length of the leaflets and/or diameter of the valve opening, have been defined to qualify for clipping treatment. However, current selection guidelines still lack prediction power with respect to complications and effectiveness of the therapy in specific patients. It is not uncommon to perform several trials during the intervention and, in some cases, decide to place two clips ($\approx 30\%$ of the patients) or even to abort the procedure due to complications ($\approx 10\%$ of the patients).

The complexity of MV anatomy and its fast dynamics make accurate quantification of the MV anatomy from medical images difficult. Ultrasound images, such as three-dimensional over time (3D+t or 4D) transesophageal (TEE), may be used to evaluate MV function in patients. 3D+t TEE ultrasound not only shows the dynamics of the structure but also enables the clinicians to compute guideline parameters. Other modalities, such as DynaCT, may be used. However, MV quantification requires tedious and time-consuming expert delineation, with little computational assistance.

More automatic methods have been proposed to make MV assessment more efficient. An interactive algorithm based on thin-tissue detection and level-set deformable models may identify the MV and the LV endocardium in 3D TEE images. Detailed geometrical models may be obtained, but several user interactions are still necessary to guide the modeling. Alternatively, the succession of mitral annulus detection and tracking, leaflet segmentation of the open valve, and leaflet tracking using a deformable model that handles contacts and chordae stresses has been proposed. Temporal re-sampling of 3D+t TEE images acquired on multiple heartbeats may improve temporal consistency. However, it is not clear how that succession of steps generalizes on large populations, with wider spectrum of MV disease, because of the numerous parameters to set.

In another approach to modeling the MV anatomy, machine learning is used to detect the MV on 3D+t TEE, computed tomography (CT) or DynaCT images. Other heart valves and papillary tips may be detected. Adding biomechanical constraints may improve the robustness of MV tracking in the presence of noise and signal drop-off in medical images.

However, quantifying the current function of the MV might not be sufficient to plan the optimal treatment for a specific patient. Computational models of MV physiology have been proposed to study MV physiology and assess how the pathological MV dynamics may be modified after intervention. Three categories of computational MV models may be identified: structural models, fluid-structure interaction models and deformable models. However, current approaches may not be computed from clinical data of large populations due to idealized framework, require tedious manual process to build the anatomical models, and suffer from a lack of integrated system for streamlined, clinical applications.

BRIEF SUMMARY

By way of introduction, the preferred embodiments described below include methods, computer readable media and systems for valve treatment simulation from medical diagnostic imaging data. Patient specific data is used to generate a model of the valve. The model may be generated from the patient specific data automatically or with minimal user indication of anatomy locations relative to an image. Any characteristics for the valve not extracted from images of the patient may be added. Added characteristics may include chordae. The characteristics may be adjusted based on user feedback and/or comparison with images of the patient. The effect of therapy on closure of the patient valve may be simulated from the model.

In a first aspect, a method is provided for valve treatment simulation from medical diagnostic imaging data. A processor estimates an anatomy model of a valve of a patient from the medical diagnostic imaging data of the patient. The processor computes a volumetric model of the valve as open. The volumetric model is a function of the anatomy model. Locations for placement of a valve clip relative to the valve are received. The processor simulates an effect of the valve clip at the locations on the valve of the volumetric model according to a biomechanical model. The processor predicts the effect of placement of the valve clip at the locations on the valve.

In a second aspect, a non-transitory computer readable storage medium has stored therein data representing instructions executable by a programmed processor for valve treatment simulation from medical diagnostic imaging data. The storage medium includes instructions for modeling closure of a valve based on scan data from a patient such that the closure is different for different patients, and simulating the closure of the valve from the modeling, the simulating including a force from therapy.

In a third aspect, a system is provided for valve treatment simulation from medical diagnostic imaging data. An ultrasound scanner is configured to scan a heart volume of a patient. The scan provides medical diagnostic ultrasound data representing a valve. A processor is configured to detect, as a function of application of the medical diagnostic imaging data to a machine-learnt probabilistic model, valve anatomy. The detection occurs during the scan. The processor is also configured to simulate closure of the valve with the valve anatomy and to simulate placement of a valve clip on the simulation of the closure. A display is configured to generate a visualization of the closure with the valve clip.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

An efficient and predictive framework may assist a surgeon in planning a mitral clip or other valve procedure and guide the surgeon during the intervention. Computational models of valve physiology are translated to clinical practice. In-vivo patient-specific data is used for clinical application with little or no time-consuming manual delineations of anatomy.

In one embodiment, an integrated system uses finite-element modeling of mitral valve biomechanics from patient specific medical images. The modeling may be used for other valves. Ultrasound, CT or DynaCT images are used, but other modalities may be used. The modeling is used for guidance of MitralClip intervention, but other types of intervention may be simulated.

The treatment of mitral valve (MV) diseases relies on comprehensive clinical evaluation and therapy personalization to optimize outcome. Finite-element modeling (FEM) of MV closure is used to study the impact of MV repair in terms of tissue biomechanics and blood flow. The MV closure modeling is based on patient-specific anatomies and boundary conditions. Starting from temporal medical images, a comprehensive model of MV apparatus dynamics, including papillary tips, is estimated using a machine-learning approach. A detailed volumetric model of the open MV at end-diastole is then computed. For the volumetric model, chordae and leaflet fibers are added to the anatomy. Using a FEM of MV biomechanics, the volumetric model operation to close the MV is computed. The locations of key components of the anatomy model may be used as boundary conditions in the FEM simulation. More especially, mitral annulus and papillary tips motions are constrained from the image data for increased accuracy. Chordae properties (rest length, stiffness and insertion points) and boundary conditions may have a significant influence upon the simulation results.

Figure 1:
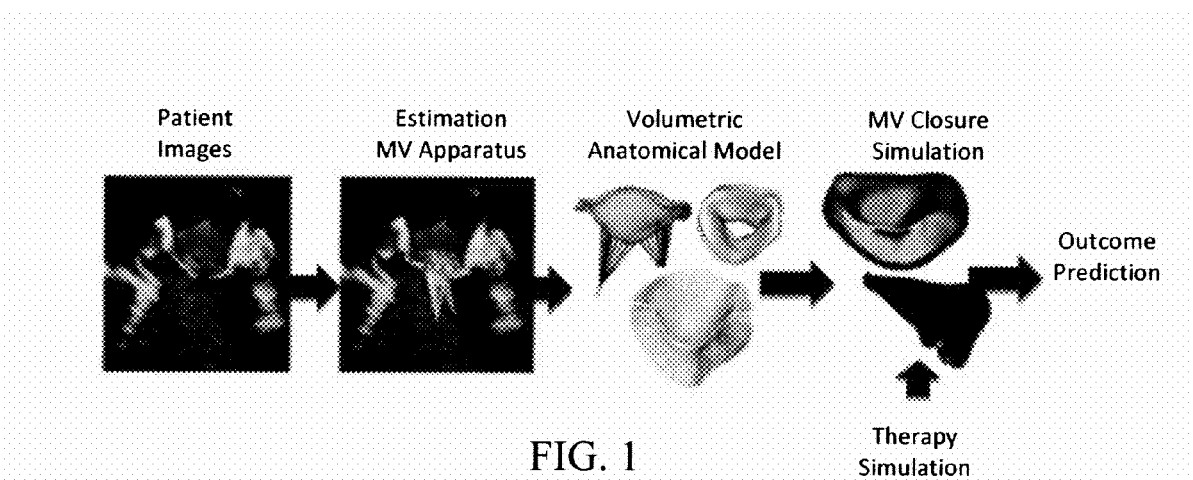
FIG. 1 is an example illustration of a framework for patient-specific valve treatment simulation from medical diagnostic imaging data.

As a first step towards patient-specific MV FEM, the proposed integrated framework combines efficient machine-learning with a biomechanical model of the valve apparatus to simulate MV function and therapies in patients. FIG. 1 shows an example of this framework for simulating the effect of therapy on MV closure. First, a comprehensive anatomical model of MV apparatus, including papillary tips, is estimated from medical images representing a particular patient. Second, a detailed volumetric model comprising leaflet fibers and chordae is automatically built. MV closure is then simulated based on a biomechanical model. After input of therapy location, the framework is applied to MitralClip planning by simulating the intervention. The output prediction may be used for treatment planning, such as attempting to locate the clip position with a more likely positive outcome in terms of residual mitral regurgitation.

Figure 2:
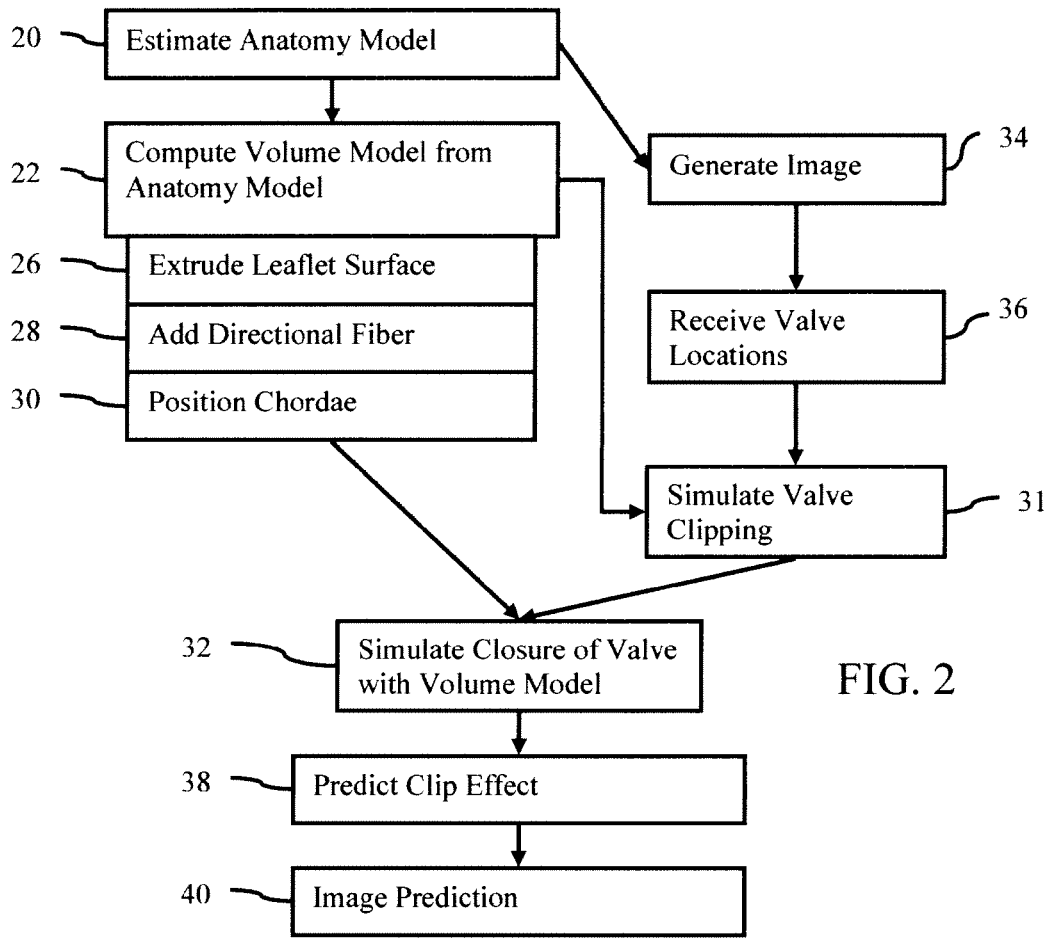
FIG. 2 is a flow chart diagram of embodiments of methods for valve treatment simulation from medical diagnostic imaging data.

FIG. 2 shows a method for valve treatment simulation from medical diagnostic imaging data. The method is implemented by a medical diagnostic imaging system, a review station, a workstation, a computer, a PACS station, a server, combinations thereof, or other device for image processing medical diagnostic data. For example, the system or computer readable media shown in FIG. 9 implements the method, but other systems may be used.

The method is implemented in the order shown or a different order. Additional, different, or fewer acts may be performed. For example, one or more of acts 26-30 are not provided. As another example, act 20 is performed without act 22 or vice versa. The location for treatment may be received from the user or automatically determined without generation of the image in act 34.

The acts are performed in real-time, such as during scanning. The user may view images of acts 34 and/or 40 while scanning to acquire another dataset representing the volume. The acts may be performed during an appointment or off-line in a review period. The images may be associated with previous performance of one or more of the acts in the same imaging session. For example, the volumetric model is generated at one time and the simulation of closure and therapy effects are performed at a different time or as part of a different review. Measurements and/or images of automatically detected anatomy may be provided in seconds, such as 10 or fewer seconds. Alternatively, the acts are performed as desired by a surgeon regardless of whether a patient is currently at the facility or being scanned.

Acts 20, 22, and 32 may be performed automatically. The user causes the patient to be scanned or obtains scan data for the patient from a previous scan. The user may activate the process. Once activated, the anatomy is identified through a sequence of images for estimating the anatomy model in act 20, the volumetric model is created from the anatomy model in act 22, and the closure of the valve is simulated in act 32 without further user input. Some user input may be provided, such as correcting the anatomy estimation if necessary, adjusting chordae properties (e.g., length) or other parameters of the model. User input of locations of the anatomy in any of the scan data may be avoided, but the user may acknowledge proper location determination by a processor and/or input anatomy relative to one or more images or the user may be provided the opportunity to edit or input locations.

The closure of a valve is modeled in act 32 based on scan data from a patient. This patient-specific modeling may capture the closure observed in each individual patient. For one patient, the closure may be incomplete, such as associated with mitral valve anomalies. For another patient, the model may indicate complete closure or failure to close at a different location. Patient-specific data alters the model.

The modeling and patient-specific fitting of the anatomical model may be performed for any heart valve. In one embodiment, a single heart valve is identified and parameterized. In other embodiments, more than one heart valve is identified and parameterized at a same time or during a same imaging session. For example, the mitral valve and the aortic valve are physiologically modeled.

For patient specific modeling, one or more sets of data are obtained. Ultrasound, computed tomography (CT) or dynaCT data is obtained. Any medical imaging modality capable of scanning a volume multiple times during a heart cycle may be used, such as TEE echocardiography. The ultrasound data corresponds to a data set interpolated to a regular 3D grid, displayed images (e.g., detected and scan converted ultrasound data), beamformed data, detected data, and/or scan converted data. The ultrasound data represents a volume or 3D region of a patient. The region includes tissue, fluid or other structures. Different structures or types of structures react to the acoustic energy differently. The shape of a structure or spatial aspect may be reflected in B-mode or harmonic data. The data represents the anatomical region of the patient.

Figure 3:
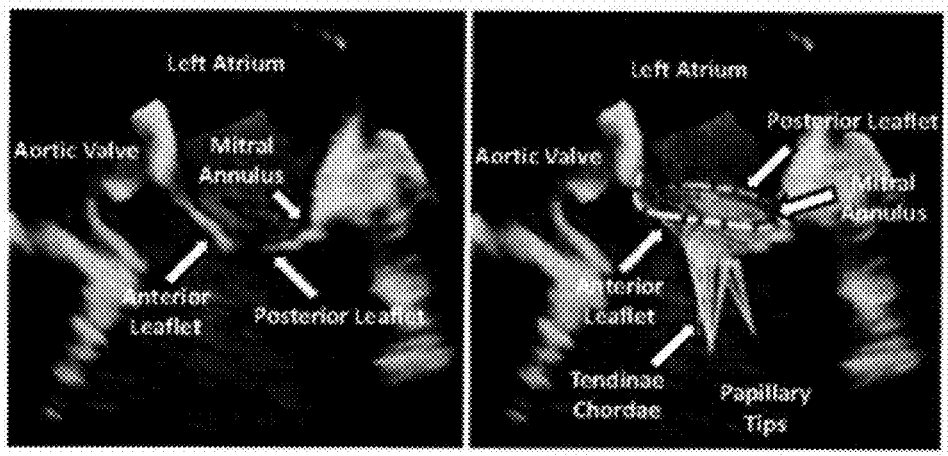
FIG. 3 shows example medical images showing mitral valve anatomy.

In act 20, a processor estimates an anatomy model of a mitral valve of a patient from the medical diagnostic imaging data of the patient. The model represents relative locations of anterior and posterior papillary tips, mitral annulus, anterior leaflet (AL) and posterior leaflet (PL). FIG. 3 shows these locations on a medical image. Additional, different, or fewer anatomic locations may be used.

For determining the location, shape, motion, size or other characteristic of a heart valve, the valve is modeled generally. The model is fit to patient specific data by estimation. Any estimation may be used, such as disclosed in U.S. Published Patent Application No. 2010/0240996 or U.S. Pat. No. 8,009, 887, the disclosures of which are incorporated by reference. The estimation is performed in sequential stages, such as associated with a hierarchal model. For example, a location of the global valve relative to the heart volume is estimated, one or more locations in the valve relative to other portions of the valve are then estimated, and a surface of the valve is then estimated. Each stage may use the same or different algorithms. For example, separate machine-learnt algorithms are used.

In one embodiment, a physiological model of the aortic and mitral valves is designed to capture complex morphological, dynamical and pathological variations. The hierarchical definition is constructed on three abstraction levels: global location and rigid motion model, non-rigid landmark motion model, and comprehensive aortic-mitral model. Along with the parameterization, an anatomically driven re-sampling method to establish point correspondence required for the construction of a statistical shape model is provided. A collision detection and repair algorithm may provide physiological consistency.

For estimating from the model relative to a particular patient, patient-specific aortic-mitral model estimation is provided. The model parameters are estimated from volumetric sequences (3D+time data) to construct patient-specific aortic-mitral representations. The estimation is from ultrasound, CT, or other data representing a volume including the valve over time. For example, MV anatomy is estimated from 3D+t TEE images.

Figure 4:
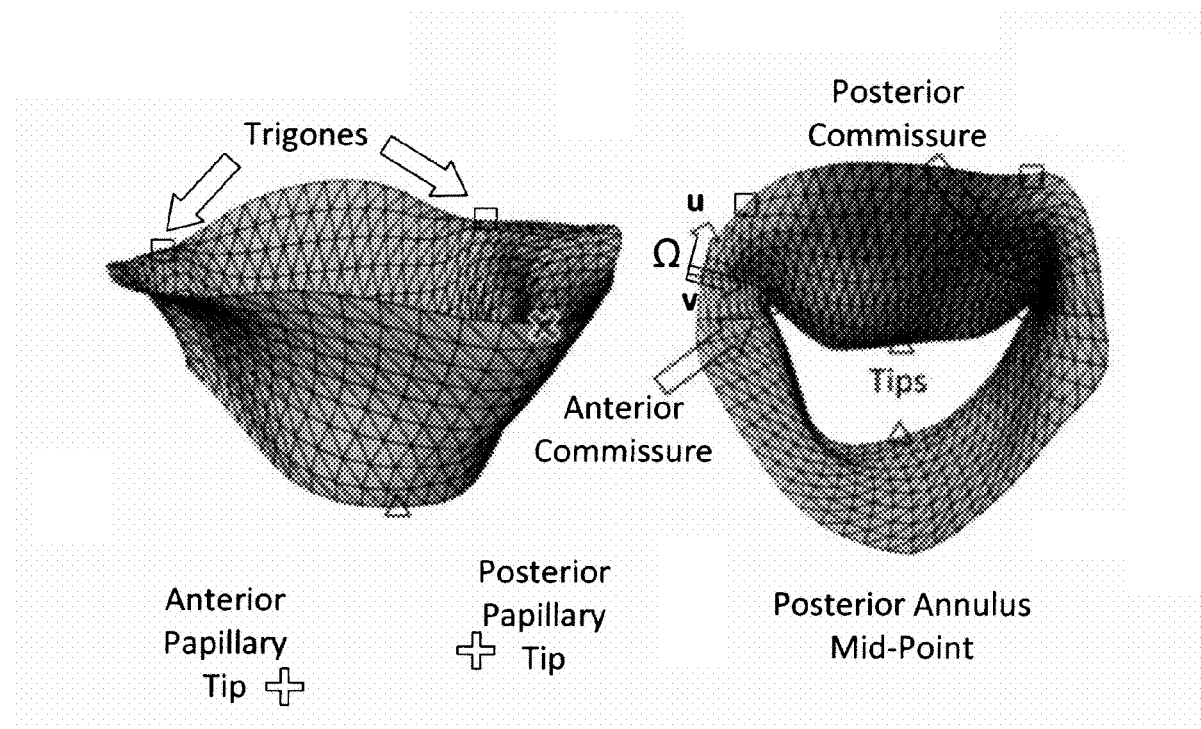
FIG. 4 is an illustration of example landmarks and mesh for a mitral valve.

To capture a broad spectrum of morphological variations, the model is parameterized by three coarse-to-fine components: i) three transformations B for global location, orientation and scale over the cardiac cycle; ii) the trajectories of ten anatomical landmarks $L(B)=(l1 \ldots l10) \in R^{3 \times 10}$ (two trigones, one posterior annulus mid-point, two commissures, two leaflet tips and two papillary tips (see FIG. 4); and iii) a triangulated surface mesh $S_{LA}(B, L)$ to represent the left atrial (LA) surface of both anterior and posterior leaflets. The positions of the vertices of the LA surface are constrained by the anatomical landmarks, resulting in an anatomically consistent parameterization $(\Omega, u, v)$ that ensures intra- and inter-patient point correspondence. As represented in FIG. 4, $\Omega$ is the vertex of the mitral annulus that is directly perpendicular to the anterior commissure, u (v, respectively). u is the curvilinear coordinate tangent (radial, respectively) or circumference, and v is the annulus to the free edge. $u_{res}$ and $v_{res}$ are the resolutions along the u and v coordinates, respectively.

This anatomy model is estimated from the patient specific data. The patient specific data is an input feature to the model, such as a machine-learned matrix. In one embodiment, B, L(B) and $S_{LA}(L, B)$ are estimated from the images using a hierarchical discriminative learning algorithm. The probability p(B, L, S/I) knowing the image data I is incrementally modeled within the Marginal Space Learning (MSL) framework, based on the Probabilistic Boosting Tree (PBT). Given a test image, the MLS framework finds position candidates around the MV based on Haar- and steerable features. The position candidates are then successively refined by rotation and scaling candidates. This defines a region of interest inside which the positions of ten landmarks are estimated using the same strategy.

Next, a point-distribution model of the MV surface is mapped according to the landmarks and deformed, within the learned space of shapes, according to boundary detectors estimated through PBT. Finally, the complete MV anatomy is tracked over the cardiac sequence using a manifold-based motion model.

A robust learning-based algorithm, which in concordance with the hierarchical parameterization, includes three stages: global location and rigid motion estimation, non-rigid landmark motion estimation and comprehensive aortic-mitral estimation. Each stage may be implemented differently. In one embodiment, trajectory spectrum learning (TSL) with local-spatio-temporal (LST) features is used for the non-rigid landmark motion estimate. The number of stages may be fewer or more. The same algorithm is used for either ultrasound or computer tomography data. Alternatively, different algorithms are trained for the different types of data.

Any machine training may be used for one or more stages. The machine-trained classifier is any one or more classifiers. A single class or binary classifier, collection of different classifiers, cascaded classifiers, hierarchal classifier, multi-class classifier, model-based classifier, classifier based on machine learning, or combinations thereof may be used. Multi-class classifiers include CART, K-nearest neighbors, neural network (e.g., multi-layer perceptron), mixture models, or others. A probabilistic boosting tree may be used. Error-correcting output code (ECOC) may be used.

The classifier is trained from a training data set using a computer. Any number of expert annotated sets of data is used. For example, about 200 hundred volume sequences representing the heart and including one or more valves are annotated. The annotation indicates valve landmarks and/or surfaces within the volumes. The different anatomies of each volume are annotated. This large number of annotations allows use of a probabilistic boosting tree to learn relevant features over a large pool of 3-D Haar, and/or steerable features. Both features may be efficiently computed and be effective as a feature space for boosting classifiers. Other features may be used. Each classifier uses the data sets and annotations specific to the anatomy being classified.

In one embodiment, the classifier is a knowledge-based probabilistic model, such as marginal space learning using a hierarchical search. A database of known cases is collected for machine learning, providing a database-driven knowledge-based approach. For training data, three-dimensional context information is preserved and guides the detection process. Knowledge is embedded in large annotated data repositories where expert clinicians manually indicate the anatomies and/or measurement indicators for the anatomies. Training and detecting the location of measurement indicators include detecting the associated anatomy since the measurement indicator indicates the anatomy. The detectors are trained on a large number of annotated 3D volumes. The classifier learns various feature vectors for distinguishing between a desired anatomy and information not being detected. In alternative embodiments, the classifier is manually programmed.

For learning-based approaches, the classifier is taught to distinguish based on features. For example, the probability model algorithm selectively combines features into a strong committee of weak learners based on Haar-like local rectangle filters whose rapid computation is enabled by the use of an integral image. Features that are relevant to the anatomies are extracted and learned in a machine algorithm based on the experts' annotations, resulting in a probabilistic model. A large pool of features may be extracted. The training determines the most determinative features for a given classification and discards non-determinative features. Different combinations of features may be used for detecting different anatomies, the same anatomy at different resolutions, and/or the same anatomy associated with different translation, rotation, or scale. For example, different sequential classification stages utilize different features computed from the 3D volume data. Each classifier selects a set of discriminative features that are used to distinguish the positive target from negatives. The features are selected from a large pool of features. The large pool is determined by a programmer or may include features systematically determined.

A tree structure may be learned and may offer efficiency in both training and application. Often, in the midst of boosting a multi-class classifier, one class (or several classes) has been completely separated from the remaining ones and further boosting yields no additional improvement in terms of the classification accuracy. For efficient training, a tree structure is trained. To take advantage of this fact, a tree structure is trained by focusing on the remaining classes to improve learning efficiency. Posterior probabilities or known distributions may be computed, such as by correlating anterior probabilities together.

To handle the background classes with many examples, a cascade training procedure may be used. A cascade of boosted binary-class strong classifiers may result. The cascade of classifiers provides a unified algorithm able to detect and classify multiple objects while rejecting the background classes. The cascade structure corresponds to a degenerate decision tree. Such a scenario presents an unbalanced nature of data samples. The background class has voluminous samples because all data points not belonging to the object classes belong to the background class. Alternatively, the classifiers are sequentially trained without cascade.

The probabilistic boosting tree (PBT) unifies classification, recognition, and clustering into one treatment. A probabilistic boosting tree is learned for each anatomy or stage of interest. The classifier is a tree-based structure with which the posterior probabilities of the presence of the anatomy of interest are calculated from given data. Each detector not only provides a binary decision for a given sample, but also a confidence value associated with the decision. The nodes in the tree are constructed by a combination of simple classifiers using boosting techniques, such as disclosed by U.S. Pat. Nos. 7,702,596 and 7,916,919.

By inputting the patient-specific data, the anatomy model is estimated for a given patient. The locations for the anatomy are estimated for a given time, such as end-diastole, and/or for a sequence of times, such as throughout a heart cycle. The anatomy model may include information not obtained from the scan data. The anatomy model may include a mesh fit to the valve based on the detected anatomy (see FIG. 4).

In act 22, a volumetric model is computed by adding information to the anatomy model. A processor computes the volumetric model. The model is of the valve in an open position (end-diastole for the mitral valve), but it can be computed from any position observed in the images. The anatomy model is used as a starting point for the volumetric model. For simulating MV closure, the volumetric model is formed by adding i) a thick, tetrahedral representation of MV leaflets, ii) MV leaflet fiber orientation to capture tissue anisotropy and/or iii) MV chordae to the anatomy model. Acts 26, 28, 30 represent these three additions to the anatomical model to form the volumetric model. Additional, different, or fewer additions may be made.

In act 26, the thick, tetrahedral representation of the MV leaflets is added. The left ventricle surface of the leaflets is obtained by extruding the estimated atrial surface towards the ventricle. The extrusion is based on images, if the thick leaflet is visible. When this is not possible, as in ultrasound images whose inconsistent quality make the accurate measurement of leaflet thickness challenging, the LV surface of the leaflets, $S_{LV}$, is computed for the volumetric model by extruding the previously estimated atrial surface $S_{LA}$ towards the ventricle. The normal to each point in the atrial surface is followed to move the surface towards the left ventricle along the normal. The surfaces $S_{LA}$ and $S_{LV}$ are merged at the free-edge and annulus to obtain the thick geometry.

Figure 10:
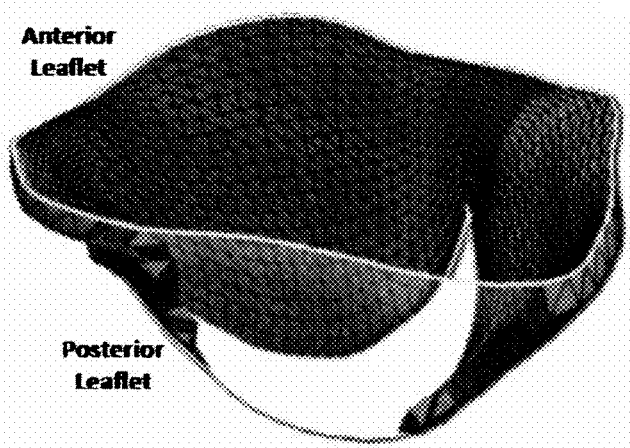
FIG. 10 illustrates an example of volumetric tetrahedral model of a mitral valve.

Leaflet thickness is controlled through the extrusion depth, such as 1.32 mm and 1.26 mm for the AL and PL, respectively. Other depths may be used, estimated from images if the thick leaflet is visible. Tetrahedral elements are created between $S_{LA}$ and $S_{LV}$ by connecting the surface vertices. FIG. 10 shows an example of tetrahedral mesh. Other volumetric meshes may be used (hexahedra, etc.). As the volumetric mesh is built from the anatomy model, the number of elements is directly controlled by the resolution of the atrial surface $S_{LA}$, $u_{res}$, and $v_{res}$, and point correspondence is ensured across time frames and patients. For regional personalization, each element is automatically tagged according to the leaflet to which the element belongs.

Figure 5:
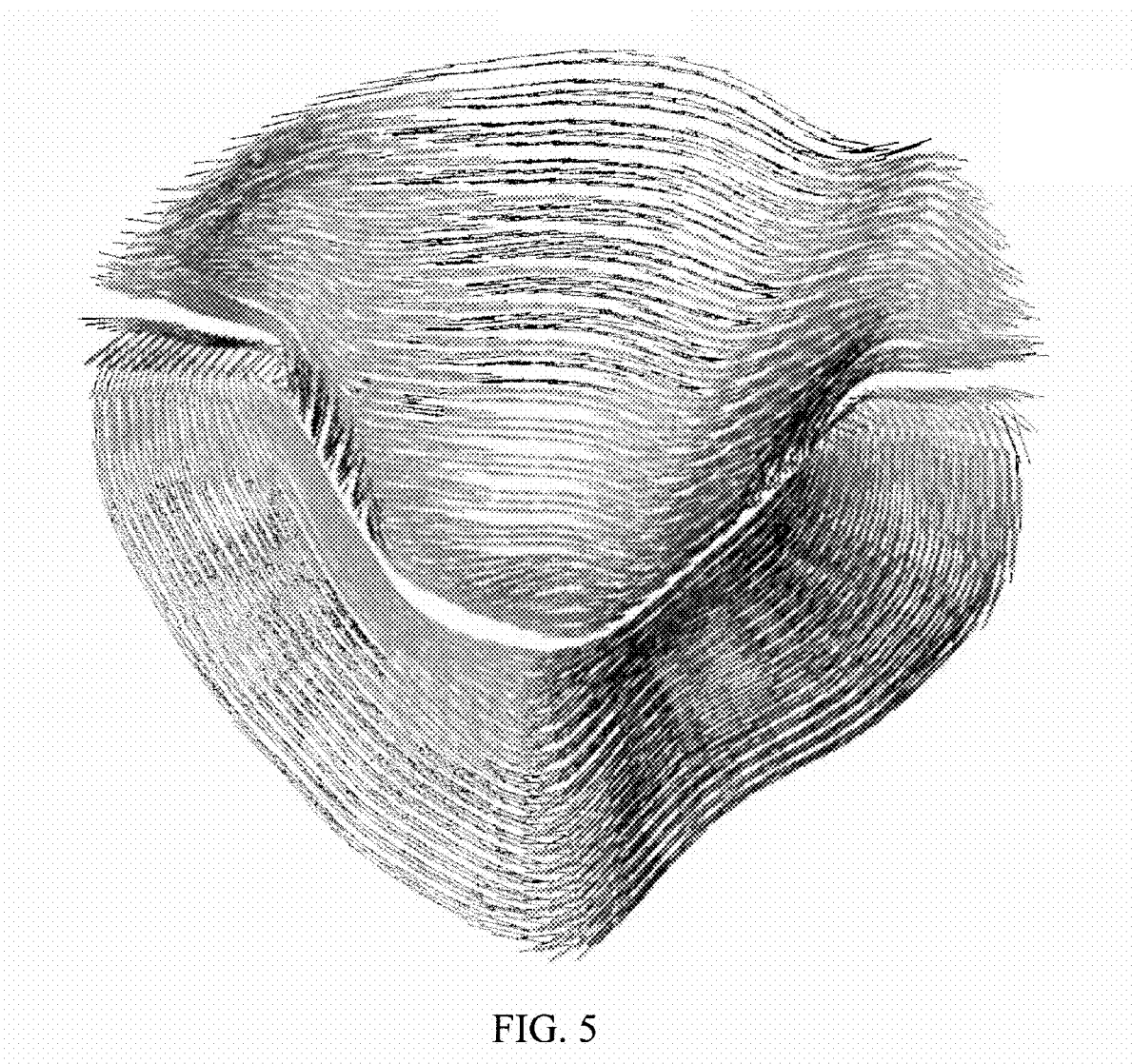
FIG. 5 illustrates example fibers for a mitral valve.

In act 28, directional fibers are added to the anatomical model. The directional fibers are added into the leaflets, one fiber direction per mesh node. Current in-vivo imaging technology may not quantify leaflet collagen fiber orientation. The direction of the fibers may be modeled. Fibers are mainly parallel to the annulus (e.g., circumferential direction). For the anterior leaflet, the fibers close to the commissures gradually rotate to become perpendicular to the annulus (radial direction). FIG. 5 shows example fibers added to the anatomy model to form the volumetric model. Any density of fibers may be added, controlled by $u_{res}$ and $v_{res}$. Any contour, mapping, or curvature of the fibers may be used, such as associated with actual tissue fibers in valves in general. Any other representation of fibers may be used, such as quadratic or bicubic interpolation throughout elements. A patient-specific measurement may be used to set the number or characteristic of the tissue fibers.

Figure 6:
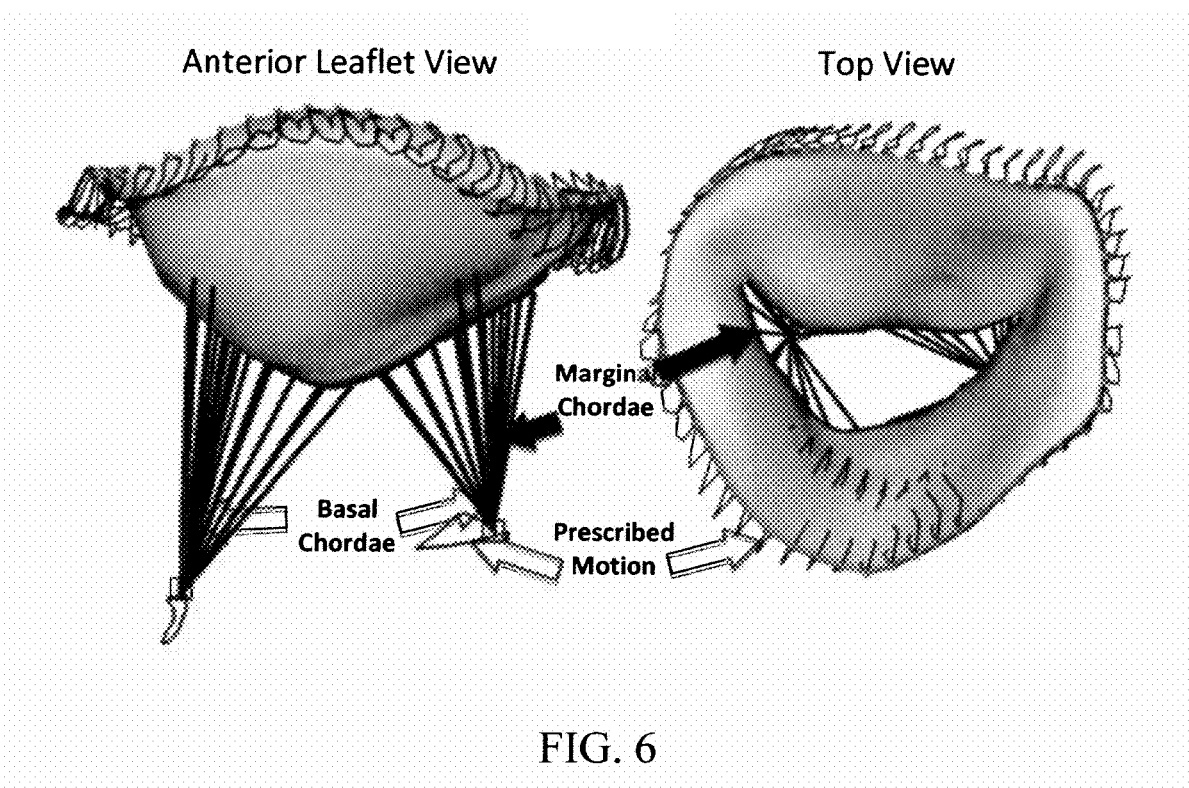
FIG. 6 shows example motion paths and chordae for a mitral valve.

In act 30, chordae are positioned in the anatomical model to form the volumetric model. The chordae add force to the motion of the valve, but may not be visible in 3D+t TEE images. Any number of chordae for interconnecting the papillary tips, attached to the left ventricle, with the mitral leaflets may be used. FIG. 6 shows one example. Twenty-eight marginal chordae are evenly attached between papillary tips and leaflet free edges. Four basal chordae are attached to each leaflet, two for each papillary tip.

To avoid any bias in the evaluation, insertion points are identical across subjects owing to the point correspondence. In one embodiment, the insertion points of the marginal chordae are defined by $(u,v)=(ku_{res}/28, v_{res}-1)$, where k includes [[0:27]]. Basal insertion points are defined by $(u,v)=((2i+1)u_{res}/8, (v_{res}-1)/2)$ and $(u, v)=((2i+1)u_{res}/8+1, (v_{res}-1)/2)$, i includes [[0:3]].

In a first embodiment, the rest length of the chordate is estimated automatically at the end-diastole frame (when the mitral valve is open), as the distance $L_0$ between the corresponding papillary tip and the leaflet insertion point.

In alternative embodiments, different numbers, lengths, and/or insertion points may be used for different patients. The characteristics of the chordae may be based on a patient characteristic or comparison of closure simulation to actual imaged closure. For example, different chordae lengths are tested in the simulation of act 32. The lengths for a given simulation are all the same or have any variance. The differences (e.g., sum of absolute positions) between the leaflet free-edges from (1) the anatomy model at closure or as detected in the scan data and (2) the simulated positions is used. By comparing the volumetric model against the medical diagnostic imaging data, different lengths may be attempted. The lengths minimizing the differences are selected. Other characteristics (number of insertion points, stiffness, etc.) may be tested, such as in an iterative approach.

In act 32, the processor simulates closure of the valve of the volumetric model with a biomechanical model. The volumetric model is generated with the valve open. To simulate closure, forces are applied to the volumetric model. The forces emulate actual forces that cause closure, such as blood pressure and muscle movement. The simulation may be for closure without the clip or treatment, may be used for closure with the clip or treatment, or may be used for placement of the clip. In one embodiment, the simulation is performed to refine the biomechanical model without clipping (act 32 without act 31), to emulate placement of the clip without progressing to biological closure (act 31), and then to emulate closure of the valve under the influence of the clip (act 32 with act 31).

The biomechanical model is a dynamics system. For example, the biomechanical model is $M\ddot{U}+C\dot{U}+KU=F_c+F_p$, where U is the displacement vector of the free vertices of the MV mesh, $\dot{U}$ is the velocity vector, and $\ddot{U}$ is the acceleration vector. M is the lumped mass matrix. Any mass matrix may be used, including uniform mass or mass with spatial variation. In one embodiment, a uniform mass density $\rho=1.04$ g/mL is used. The mass parameter can be set by the user. K is the stiffness matrix of the internal elastic forces. C is a Rayleigh damping matrix defined by $C=0.1M+0.1K$. $F_c$ and $F_p$ are the forces developed by the chordae and heart pressure, respectively. Additional, different, or fewer forces may be used. Other representations of the biomechanical model may be used, such as quasi-static analysis.

In one embodiment, the leaflets are modeled as linear, transverse isotropic elastic tissues. Leaflets may behave as linear materials in the range of physiological pressures even if modeled throughout the cycle. Moreover, linear elasticity models are also computationally efficient, allowing fast simulations and real-time intervention planning. In one embodiment, the model is solved using co-rotational linear tetrahedral finite elements to cope with large deformations and rotations. However, in alternative embodiments, more detailed leaflet models, such as non-linear hyper-elasticity, may be used.

Different or the same tissue properties are assigned to the AL and PL, such as AL Young's modulus of $E_{ALf}=6.233$ MPa, $E_{ALf\perp}=2.350$ MPa, AL shear modulus of $G_{ff\perp}=1.369$ MPa, PL Young's modulus of $E_{PLf}=2.087$ MPa, $E_{PLf\perp}=1.887$ MPa, and PL shear modulus of $G_{ff\perp}=0.694$ MPa. Other values representing the tissue may be used. The perpendicular indication is relative to the fiber direction.

Figure 7:
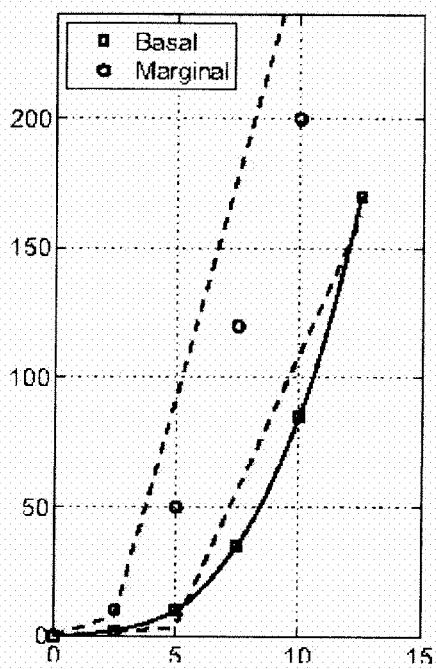
FIG. 7 is a graph showing linear approximation of stress-strain behavior of chordae, according to one embodiment.

For the biomechanical model to simulate closure, the chordae are modeled as piecewise tensile springs. The springs are between papillary tips, modeled as spatial points, and leaflet insertion points. Between an insertion point $v_i$, i including (marginal, basal) and its corresponding papillary tip $p_i$, the applied force is: $f_c(v_i,p_i,t)=-k_{c,i}(\epsilon_{c,i},t)\times(L_i(t)-L_{i,0})$, where $\epsilon$ is the strain, $L_i$ is current elongation $\|v_i(t)-p_i(t)\|$, and $L_{i,0}$ is the chordae rest length. The chordae rest length is the distance between the papillary tips and the insertion points estimated at the mid-diastole time frame. The stiffness $k_{c,i}(c,i,t)$ depends on the strain $\epsilon_{c,i}(t)=(L_i(t)-L_{i,0})/L_{i,0}$ to model the non-linear response of the chordae. At compression, $\epsilon<0$, $k_{c,i}=0$ g/mm (free compression). At low tension, chordae exhibit low stress, which then increases dramatically and almost linearly as shown in FIG. 7. Spring tensile stiffnesses, $k_{c,i}$, are calculated from the chordae Young moduli according to $k_{c,i}=A_{0,i}E_{c,i}/L_{0,i}$, where $A_{0,i}$ is the chordae cross-section at rest. Example parameters characterizing the chordae are shown below:

| | |
|---|---|
| Young's modulus (E < 2.5%) | $E_c$ = 312 g/mm2 |
| Young's modulus (E ≥ 2.5%) | $E_c$ = 3406 g/mm2 |
| Cross-section | $A_0$ = 0.40 mm2 |
| Young's modulus (E < 5%) | $E_c$ = 66 g/mm2 |
| Young's modulus (E ≥ 5%) | $E_c$ = 2120 g/mm2 |
| Cross section | $A_0$ = 2.05 mm2 |

Other values may be used. More detailed, non-linear models may be used.

Given the chordae and leaflet properties, the force from pressure and the chordae are applied to the volumetric model with the biomechanical model. The solution for the simulation is performed with boundary conditions for motion of mitral annulus and papillary tips. The positions of mitral annulus and papillary tips at different times are provided from the anatomical model. These positions are prescribed from patient-specific image or scan data.

The motion of the papillary tips and of the mitral annulus is prescribed from the automatic detection of the anatomical model. FIG. 6 shows example motion of these anatomic portions as curves overlaid on the valve representation. In practice, the displacement and velocity of the prescribed vertices are projected at every time step of the simulation such that the simulated velocity and displacement correspond to the motion observed in the images. Correct valve closure may depend on the papillary positions and the shape of the annulus during systole.

The position of the leaflets is limited to avoid collision. While contact may be allowed, a collision leading to a portion of one leaflet being in another leaflet is prevented in the simulation. Self-collisions are detected using a ray-casting approach. Leaflet-leaflet interactions in the normal direction (along the rays) are handled using a penalty constraint. For example, within 0.5 mm, a spring is created to prevent crossing. Longitudinal shifting, such as associated with friction sliding against each other, is not prevented. Tangential interaction is modeled with a friction coefficient of 0.1. Other friction coefficients may be used.

Valve biomechanics are simulated between the end of diastole and beginning of iso-volumetric contraction. The valve just closes at the beginning of iso-volumetric contraction. Other periods may be simulated. In particular, the proposed embodiment may be applied for full cardiac cycle simulation.

By applying a generic profile for pressure that increases from 0 mmHg to 120 mmHg for the blood pressure, the simulation is performed. Any profile for pressure may be used, such as a measured or assumed profile. For example, an exponential curve going rapidly from 0 mmHg pressure, 0 normalized time to about 100 mmHg at about 0.19 normalized time and then approaching about 120 mmHg at about normalized time of 1.0. In another example, a pressure profile measured for the specific patient is directly used.

The simulation is performed by solving the biomechanical model using the finite element method. The various components are spatially and temporally handled in discrete steps. After discretization, the dynamics system amounts to a linear system whose unknowns are the new positions of the volumetric model vertices.

The finite element modeling is performed without user input of anatomy locations other than for locations of application of a clip in the therapy. The user may activate the creation of models and simulation, but input of locations of anatomy is avoided. The simulation is performed automatically. In alternative embodiments, the user confirms or indicates locations of anatomy for creation of models or control of the closure simulation.

In act 34, an image of the valve is generated. The image is from the acquired scan data, from the anatomy model, and/or from the volumetric model. For example, the position of anatomy of the valve with the valve as open is determined and used to generate an image. In another example, the mesh representing the valve may be used for imaging. Alternatively, the scan data from the time (e.g., end diastole) at which the valve is open and beginning to close is used. The image may be dynamic, showing the motion of the valve. The user can interact with the imaging processor, to choose the view and orientation.

Figure 8:
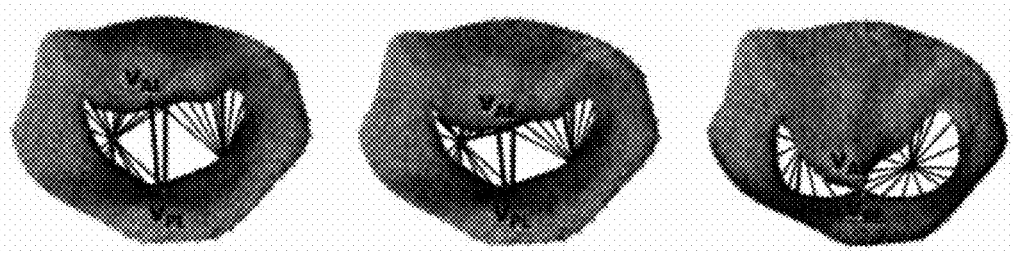
FIG. 8 shows example simulated valves with clipping in one embodiment.

The image is a rendering of a three-dimensional volume. Voxels or data representing three-dimensional locations are rendered to a two-dimensional view. The viewing direction is from the left atrium looking at the valve. FIG. 8, left most representation of the mitral valve, shows the view. Other viewing directions may be used and chosen interactively by the user. Ray casting, projection, surface or other rendering may be used.

As shown in FIG. 8, the chordae as positioned are included in the rendering. The fibers may similarly be included. In other embodiments, the image is generated without the chordae and/or fibers. Similarly, the mesh may be shown, not shown, or used for mapping textures.

In act 36, locations for the placement of a valve clip or other therapy are received. The locations are represented in FIG. 8, left most representation, as solid, thick black lines. This represents placement of two clips. Any number of sutures or other devices may be represented.

The locations are received form the user. For example, the user views images rendered from the scan data or the estimated model in act 20. The simulated valve in act 32 may alternatively be used for rendering. After viewing, the user selects one or more locations to apply clips. The user picks successively two vertices on each leaflet ($v_{AL}$ and $v_{PL}$). Other numbers of vertices may be selected. The selection is done interactively.

In another embodiment, the locations are received from a process or processor. For example, clips arranged at various locations are tested to identify one or more recommended locations. The recommended locations may then be presented to the user. The desired locations may be ones at which full closure is provided with minimal friction. Other criteria may be used.

In an alternative embodiment, the locations are received from a physical probe, corresponding for instance to the current location of the clip device in the patient during the therapy.

In act 31, the leaflets of the volumetric model are deformed according to the received clip locations. The deformations are computed according to the biomechanical model. The simulation includes a force or constraint based on the clip or therapy. The user may select an amount or type of force. Alternatively, the amount and/or type are assigned or predetermined. In one embodiment, the clip is modeled as a stiff spring ($k_{clip}$=1000 g/mm) between the two vertices to hold the leaflets together.

The middle representation of FIG. 8 shows the clip treatment modeled as a spring. A spring is created between the picked vertices. The force from the spring acts to draw the leaflets together. The force from the spring progressively stitches the leaflets together as closure is simulated (see FIG. 8, right most representation).

In one embodiment, simulation of valve clipping is achieved with unchanged tissue properties, but pressures are disabled and mitral annulus and papillary tips are fixed to facilitate the virtual mitral clipping. The boundary conditions are frozen such that the mitral annulus and papillary tips do not move. The leaflets are allowed to move with or without corresponding boundary conditions. Other approaches may be used, such as allowing all the boundary conditions to operate and move. The pressure may also be included to reproduce the intraoperative conditions.

Act 32 may be repeated with the clip placed. The simulation is repeated with the valve clip modeled between leaflets at the locations. Alternatively, act 32 is performed, at least initially, only after placement of the clip.

In act 38, the processor predicts the effect of placement of the valve clip or therapy on the valve position and in terms of regurgitation. By performing the simulation of act 32 with the treatment locations designated, the effect of placement is simulated. Using the volumetric model as applied to the biomechanical model, the closure of the valve with the treatment is simulated.

The simulation and prediction may be done interactively and/or iteratively. For example, virtual mitral clipping is performed interactively, in real-time, on the preoperative volumetric model as pictured in FIG. 8. On the open anatomy, the user successively picks a vertex on each leaflet in act 36. The leaflet deformations are computed according to the biomechanical model.

The framework may be performed for postoperative analysis. By running the simulation with the simulated clip, the success or not of the therapy on the patient may be modeled. In a first embodiment, the ventricle motion may be similar to the preoperative motion, as only the morphology of the leaflets changed. Accordingly, the same anatomical model as from preoperative scanning may be used. Preoperative boundary conditions and ventricular pressures are applied on the clipped geometry to simulate closure. Alternatively, a new anatomical model and ventricle motion is estimated. Possible validation may be achieved by comparing simulation outcomes with patient specific data representing the valve operating with the treatment.

In act 40, an image is generated. The image is generated from the volumetric model as simulated in response to the biomechanical model. The image represents the simulation at one time, such as at initial closure or at the time of greatest closure. A series of images may be generated representing the simulation at different times. The user can interact with the images to select the optimal view.

The mesh determined by the finite element modeling may be used to surface render the valve. The mesh is an outline or surface, but other outlines, such as interconnected landmarks, may be displayed. In alternative embodiments, the image is of the landmarks or a representation of a valve fit to the mesh or landmarks.

In one embodiment, the simulated information is overlaid on a rendering of the heart or valves. The valve images are rendered from medical data with a same scale and perspective as an outline overlaid on the rendering. Color coding or other display modulation may be used with or in addition to an overlay. For example, different surfaces of the valve are rendered from B-mode data in gray scale with color modulation specific to the simulated surface. One surface may be rendered in one color and another in another color.

One rendering or multiple renderings from the same volume may be displayed. In one embodiment, a sequence of images is displayed. The sequence is rendered from the different volumes throughout a portion (e.g., simulating closure) or entire heart cycle. For each image in the sequence, the corresponding detected or estimated valve information is displayed. The surface corresponding to the valve at the given time represented by an image is displayed. The images of the sequence may be displayed in succession to show or represent the motion of the valve. The representation of the valve is generated as a function of the surfaces simulated through the sequence.

Any type of rendering of the mesh and/or the view from the medical data may be used. Surface, projection or other rendering may be used. Planar reconstructions may be used.

The simulation without the treatment may be compared with the anatomy model created from patient-specific scan data. The generalization of the biomechanical model is tested to assess how accurately MV closure may be simulated by using patient geometry and boundary conditions but standard tissue parameters. To that end, MV closure may be simulated on multiple (e.g., 25) patients and compared with the volumetric model estimated from the images at the same time. In a first embodiment, the mean point to mesh error may be around 1.49±0.62 mm.

This error may be reduced by personalizing characteristics of tissue biomechanics. A sensitivity analysis may be performed to determine characteristics that may be changed for more accurate modeling. Similarly, the predictive power of the simulation with treatment may be tested against a patient that has undergone the treatment with the clip in the same position. By providing an integrated way to perform MV simulation, the proposed system may constitute a surrogate tool for model validation and therapy planning.

The simulation time is scaled such that the simulated MV closure is ten times longer than what is observed in the images (e.g., from 70 ms to 150 ms). The time step may be dt=0.01 seconds or other step size. The number of discrete temporal steps is increased by ten times as compared to the acquisition of scan data for the volume. The purpose of the time scale may handle the strong and discontinuous contact forces.

An implicit Euler solver is used to update mesh positions. The mesh resolution may be $u_{res}=v_{res}=30$. The number of marginal chordae may be 28. The number of basal/strut chordae may be 4. The $k_{clip}$ value may be 1000 g/mm.

In a first embodiment, the accuracy of the anatomical model may be evaluated in 200 or other number of 3D+t TEE images from 120 or other number of patients with a wide range of diseases (MV prolapse, calcified mitral annulus, stenosis, ventricular dysfunction, or others). Images are acquired with different angulation, field of view and resolution (spatial and temporal). Three-fold cross-validation against manual delineation may yield a point-to-mesh error of 2.75±0.86 mm. Qualitative evaluation may show that the algorithm tracks the MV throughout the cardiac sequence, even during valve closure and opening when the dynamics are fast. Computation time may be 4.8 seconds per 3D volume on a standard desktop machine (e.g., Intel Core2Duo, 2.66 GHz quad core, 2 GB RAM).

Evaluation of MV closure simulation may be performed in one embodiment, and FEM convergence may be analyzed. In particular, the spatial resolution and temporal time step that is required for computationally efficient but accurate simulations may be determined. Accuracy may be measured as the difference between the simulation at a given spatial/temporal resolution and the result obtained at the finest discretization. Sub-millimetric or other magnitudes of errors may be considered as satisfactory in comparison with image resolution (typically ≈0.75-1.58 mm). The analyses may be performed using the MV anatomy and boundary conditions of one or more patients with the tissue parameters discussed above. MV closure may be simulated from the volumetric model computed from the last frame where the valve was fully open (end-diastole). Simulation time may be synchronized with patient data.

Spatial convergence may be analyzed. In a first embodiment, $v_{res}=30$ may be fixed, and MV closure simulated with ures=30, 40, 50 corresponding respectively to 9408, 12768, and 16128 elements with 1.67 mm, 1.24 mm and 0.98 mm average edge-length. Qualitatively, $u_{res}$ may have little effect on the simulation result, so the lower resolution may be used. This observation may be confirmed quantitatively by measuring the point-to-mesh error with respect to the result obtained with $u_{res}=50$ ($e_{u_{res}=30}=0.43\pm0.22$ mm, $e_{u_{res}=40}=0.43\pm0.19$). $u_{res}=30$ or other values may be used to maximize computational efficiency. With $u_{res}=30$ fixed, $v_{res}=10, 20, 30$ is tested, corresponding respectively to 2688, 6048 and 9408 elements with 4.89 mm, 2.49 mm and 1.67 mm average edge-length. In that case, significant differences may result. Point to mesh error with the result obtained with $v_{res}=30$:$e_{v_{res}=10}=0.51\pm0.51$ mm). In particular, the posterior leaflet may end in a totally different position. Results at $v_{res}=20$ and $v_{res}=30$ may significantly closer to each other ($e_{v_{res}=20}=0.30\pm10.18$ mm), suggesting convergence at $v_{res}=30$. Those results may also hold for non-reported simulations at higher $v_{res}$ and $u_{res}>30$.

In temporal convergence analysis, the Euler implicit scheme theoretically allows large time steps dt. However, collision detection may be hampered if dt is too large. The effects of time discretization on the simulation results may be analyzed by computing MV closure with $dt=10^{-1}$ s, $10^{-2}$ s, $10^{-3}$ s and $10^{-4}$ s. $u_{res}$ and $v_{res}$ are set to 30. In a first embodiment, convergence may be reached at $dt=10^{-3}$ s (mean error: 0.02±0.0.02 mm, maximum: 0.11 mm). $dt=10^{-2}$ s may yield sub-voxel accuracy (mean error: 0.18+/-0.12 mm, maximum: 0.64 mm), but dt=0.1 s may be too large to reach convergence (mean error: 1.17±1.25 mm, maximum: 5.72 mm). The leaflets may not have time to close. In light of these results, $dt=10^{-2}$ s may be used for simulations.

The sensitivity of the framework with respect to boundary conditions and chordae configuration may also be analyzed. These parameters may influence the simulations. In a first embodiment, spatial resolution may be $u_{res}=v_{res}=30$ and time discretization dt=0.01 ms.

The importance of boundary conditions on the computed MV closure may be analyzed by performing the simulation with fixed mitral annulus and papillary tips. First results showed that the MV may not close anymore and may not be accurate compared to the model estimated from the images at the same time point. Mitral annulus deformation helps the leaflets to close and papillary tips are synchronized with the annulus to ensure closure. Estimation of patient-specific boundary conditions and their integration into the biomechanical model is therefore important.

The MV model uses 28 marginal chordae evenly attached to the free edges in one example. Chordae distribution may change from patient to patient. The impact of the number of marginal insertions points on the simulation may be determined by computing MV closure with 56, 28, 20, 16 and 12 marginal chordae evenly attached to the free edges. The number of marginal chordae may modify the dynamics of the leaflets. In particular, MV free edges may be closer to the mitral annulus as the number of chordae decrease, as quantified by the distance of the leaflet tips to the annulus plane defined by the trigones and the posterior midpoint. Leaflet speed may also be higher with fewer chordae as the leaflet may be less tight and more flexible under pressure.

Marginal chordae rest length $L_{i,0}$ may also have an influence on the MV dynamics. $L_{i,0}$ being the distance between papillary tips and insertion points at end diastole may underestimate $L_{i,0}$ if the chordae fold. The impact of that parameter may be determined by computing MV closure with $L_{i,0}\pm10\%$, 20% and 30%. A first experiment may result in variations of the same order of magnitude as those obtained by varying the number of chordae. The longer the rest length, the higher the leaflets go towards the annulus plane. A change of 30% in rest length may result in ≈38% and ≈1.1% change in the position of the anterior and posterior tips, respectively. This may be about an 8 mm difference for the AL. Moreover, the abrupt change in the dynamics observed with a rest length of 110%, and not elsewhere, illustrates that modifying the rest length may bring new collisions between the AL and PL, modifying the end result. Patient-specific adjustment of chordae rest length may aid simulation.

The sensitivity of the simulation with respect to chordae stiffness may be determined by computing MV closure with stiffness spanning from +/-30% of the standard values. The variations may be lower compared to the chordae length and number of chordae (e.g., ≈11% and ≈2.1% in leaflet tip positions, less than 2 mm overall). Both number of chordae and rest length parameters may have similar effects on the simulated MV dynamics. This may suggest the following personalization strategy: fixing the number of chordae for all patients, and then setting the rest length such that the position of the free edges matches what is observed in the images. An automated optimization may be run to determine the chordae length appropriate for a given patient. Alternatively, the number of chordae and/or their stiffness is changed instead or in addition to length.

The biomechanical model generalization may be evaluated with respect to tissue properties. The generalization of the biomechanical model in terms of tissue parameters may be evaluated for any number of patients. In a first embodiment, 25 or other number of randomly selected patients representing a large spectrum of heart diseases (MV diseases, aortic valve diseases, myocardium infarction, etc.) may be selected. For these patients, standard 3D+t TEE images of the MV are acquired (e.g., image resolution: 0.75-1.58 mm isotropic, 7-28 (median: 14) time frames). The dynamic models of MV anatomy may be automatically estimated on all time-frames of the sequences. To minimize bias in the evaluation of the simulation due to model estimation errors, an expert may verify the anatomical models and correct them manually whenever needed. Papillary tips may be verified.

The anatomical model at the time frame just before closure may be used to simulate MV closure. The motions of the mitral annulus and papillary tips estimated from the images may be used as boundary conditions. The pressure profile is applied. The simulated closed valve may be compared to the MV geometrical or anatomical model estimated at closure (e.g., iso-volumetric contraction). This is used as a ground truth.

Testing against the ground truth may indicate different approaches. The stimulation result may be improved by personalizing chordae rest length. Pressure distribution behind the PL may not be uniform, so a non-uniform pressure distribution may be modeled. FSI studies considering the whole cardiac chamber might be used to develop a model. Different chordae distribution may be used for the PL. PL anatomical model may not be detailed enough, so more explicit modeling of PL cleft may be used.

By manually or automatically adjusting chordae rest length based on the dynamic image data, the optimal rest length may be estimated. Point-to-mesh errors may be used to measure the difference between observed closed valve and simulated closed valve. Adjusting chordae rest length may enable improved accuracy of MV closure prediction. Further improvement may be reached by adjusting all parameters at once through inverse problem algorithms.

The ability of the framework to predict the outcome of MV intervention may be tested based on preoperative data only. In a first embodiment, simulation of MV closure based on the images before clip release may yield satisfactory accuracy after slight personalization of chord rest length (10% higher than the distance between papillary tips and leaflet free edges measured at end diastole). Point to mesh error between the simulation and the model estimated from the images at the same time point may decrease from 1.43±0.96 mm to 1.12±0.80 mm after chordae length personalization. The MitralClip intervention may be simulated on the pre-clip anatomy. The virtual intervention may be performed in real-time, such as at 2 frames or volumes per second. Applying the pressure profile on the ventricular surface and the preoperative boundary conditions (mitral annulus and papillary tips motion) may be used to predict MV closure just after release of the device (e.g., just after clipping). Biomechanical parameters may be kept constant. The model may be able to simulate MV closure after the intervention with results similar to what is observed in the post-clip-release images, suggesting promising prediction power.

Relying on a modular platform (e.g., anatomical model, volumetric model, and biomechanical model) may allow changing the framework with more detailed models to quantify the added value in terms of MV closure prediction. For example, leaflet stiffness may vary during the cardiac cycle. The model may be adjusted to account for such variance. As another example, active stiffening may contribute to the funnel shape of the anterior leaflet at systole. This feature may be integrated to improve the accuracy of the predictions in that region.

Ventricular pressure may change after mitral regurgitation repair. Myocardium force may increase, and thus the ventricular pressure may increase to preserve stroke volume. As a result, mitral annulus motion may change although only leaflet morphology is affected by the intervention. An integrated LV/MV model may increase prediction accuracy at the price of additional parameters to adjust related to ventricular biomechanics.

In a first embodiment, MV closure is considered to predict residual regurgitation after therapy. Alternatively, full cycle simulation may be considered to provide insights on the entire MV dynamics and tissue stresses for long term therapy prognosis.

Figure 9:
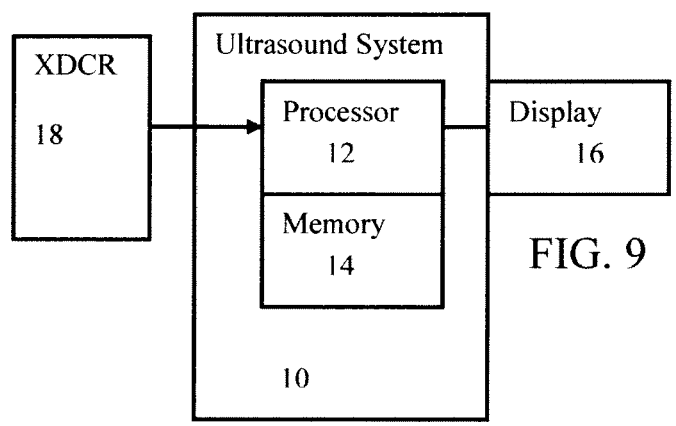
FIG. 9 is a block diagram of one embodiment of a system for valve treatment simulation from medical diagnostic imaging data.

FIG. 9 shows a system for valve treatment simulation from medical diagnostic imaging data. The system includes a transducer 18, an ultrasound scanner 10, and a display 16. The ultrasound scanner 10 includes a processor 12 and a memory 14. In alternative embodiments, the system is a CT scanner, a dynaCT scanner or system. In yet other embodiments, the system is a workstation, computer, or server for simulating using data acquired by a separate system in real-time or using previously acquired patient-specific data stored in a memory. For example, an ultrasound scanner 10 is provided for acquiring ultrasound data representing a volume, and a separate database, server, workstation, and/or computer is provided for simulating. Additional, different, or fewer components may be used.

The ultrasound scanner 10 includes a transmit beamformer, receive beamformer, B-mode detector, Doppler detector, harmonic response detector, contrast agent detector, scan converter, filter, combinations thereof, or other now known or later developed medical diagnostic ultrasound system components. As another example, the transducer 18 is not provided, such as where the system is a workstation for offline or later measurement of valve anatomy.

The transducer 18 is a piezoelectric or capacitive device operable to convert between acoustic and electrical energy. The transducer 18 is an array of elements, such as a multidimensional or two-dimensional array. Alternatively, the transducer 18 is a wobbler for mechanical scanning in one dimension and electrical scanning in another dimension. In another embodiment, the array is a one-dimensional array on a cardiac catheter or a TEE probe. Multi-dimensional arrays or a plurality of one-dimensional arrays may be provided on a TEE probe.

The ultrasound scanner 10 uses the transducer 18 to scan a heart volume of a patient. Electrical and/or mechanical steering allows transmission and reception along different scan lines in the volume. Any scan pattern may be used. For example, a plurality of different planes through the heart is scanned by rotating a TEE array, moving a catheter array, or volume scanning with a matrix array. In one embodiment, the transmit beam is wide enough for reception along a plurality of scan lines. In another embodiment, a plane, collimated or diverging transmit waveform is provided for reception along a plurality, large number (e.g., 16-64 receive beams), or all scan lines.

The scan provides the medical diagnostic ultrasound data representing the heart or valve volume at different times as a sequence. The scan is repeated to provide data for the volume at different times. Ultrasound data representing a volume is provided in response to the scanning. The ultrasound data is beamformed, detected, and/or scan converted. The ultrasound data may be in any format, such as polar coordinate, Cartesian coordinate, a three-dimensional grid, two-dimensional planes in Cartesian coordinate with polar coordinate spacing between planes, or other format. The ultrasound data may be of any type, such as B-mode, flow mode, Doppler mode, contrast agent, harmonic, or other ultrasound modes of imaging.

The memory 14 is a buffer, cache, RAM, removable media, hard drive, magnetic, optical, database, or other now known or later developed memory. The memory 14 is a single device or group of two or more devices. The memory 14 is shown within the system 10, but may be outside or remote from other components of the system 10.

The memory 14 stores the ultrasound data, such as ultrasound data representing a heart or valve volume at different times in a heart cycle. The heart volume includes at least one valve, but other portions of the heart may be represented. The memory 14 stores flow (e.g., velocity, energy or both) and/or B-mode ultrasound data. Alternatively, the medical image data is transferred to the processor 12 from another device. The medical image ultrasound data is a three-dimensional data set, or a sequence of such sets. The data represents a three-dimensional region. Any format may be used, such as voxels interpolated to a three-dimensional grid or data representing parallel or non-parallel planes.

For real-time imaging, the ultrasound data bypasses the memory 14, is temporarily stored in the memory 14, or is loaded from the memory 14. Real-time imaging may allow delay of a fraction of a second, or even seconds, between acquisition of data and imaging with measurements. For example, real-time imaging is provided by generating the images substantially simultaneously with the acquisition of the data by scanning. While scanning to acquire a next or subsequent set of data, images and measurements are generated for a previous set of data. The imaging occurs during the same imaging session or patient appointment used to acquire the data. The amount of delay between acquisition and imaging for real-time operation may vary, such as a greater delay for initially locating valve anatomies with less delay for measurements. In alternative embodiments, the ultrasound data is stored in the memory 14 from a previous imaging session and used for measuring and/or generating a planar reconstruction without concurrent acquisition.

The memory 14 is additionally or alternatively a non-transitory computer readable storage medium with processing instructions. The memory 14 stores data representing instructions executable by the programmed processor 12 for valve treatment simulation from medical diagnostic imaging data. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 12 is a general processor, digital signal processor, three-dimensional data processor, graphics processing unit, application specific integrated circuit, field programmable gate array, digital circuit, analog circuit, combinations thereof, or other now known or later developed device for processing medical image data. The processor 12 is a single device, a plurality of devices, or a network. For more than one device, parallel or sequential division of processing may be used. Different devices making up the processor 12 may perform different functions, such as an automated anatomy detector and a separate device for performing measurements associated with the detected anatomy. In one embodiment, the processor 12 is a control processor or other processor of a medical diagnostic imaging system, such as a medical diagnostic ultrasound imaging system processor. The processor 12 operates pursuant to stored instructions to perform various acts described herein, such as obtaining data, detecting anatomy, measuring anatomy, and/or controlling imaging.

In one example embodiment, the processor 12 and memory 14 are part of a desktop computer, such as a personal computer with an Intel Xeon, 2.40 GHz octocore and 4 GB RAM. This example may be able to perform the simulation, including estimation of the anatomy model, creating of the volumetric model, and application of the biomechanical model. On a single core processor, the simulation may be about ≈10 min of computation time (rate of about 0.3 frames per second, fps). The entire process, from the 3D+t TEE images to the simulation, may take about 12 min. Other amounts of processing time may be provided, such as less or more than 12 minutes, according to mesh resolution ($u_{res}$, $v_{res}$), time step, and other settings.

The processor 12 is configured to detect valve anatomy and motion. The valve motion is detected as a function of application of the medical diagnostic imaging data to a machine-learnt probabilistic model. The valve motion in represented in the sequence from the medical diagnostic imaging data. The detection occurs during a scan of a patient for feedback while the patient is being scanned or at the medical facility. Detection may occur at other times.

In one embodiment, the processor 12 is configured to detect the valve motion by simultaneously solving for location and motion of a landmark. A spectral trajectory model is applied as a machine-learnt probabilistic model. The landmark location may be estimated without other estimation. In another embodiment, a hierarchal model is used by the processor 12 to estimate global motion assuming a rigid heart valve, then non-linear motion of landmarks of the heart valve, and then a surface of the heart valve.

The processor 12 may perform machine learning and/or applies a machine-learnt algorithm. For example, the processor 12 applies a probabilistic model to detect valve anatomy.

The probabilistic model is a machine-learned classifier. Any classifier may be applied, such as a model-based classifier or a learned classifier (e.g., classifier based on machine learning). For learned classifiers, binary or multi-class classifiers may be used, such as Bayesian or neural network classifiers. The classifier is instructions, a matrix, a learned code, or other software and/or hardware for distinguishing between information in a medical image.

The classifier may include a plurality of models or classifiers (e.g., detectors) operable together or independently. For example, different probabilistic models are trained for different anatomy or types of motion. The probabilistic models may be joint or dependent. The location of other anatomies is used to limit or define a search space for a current anatomy and/or as a feature input for classification of another anatomy.

The different classifiers for joint classification, marginal space classification, and/or multiple resolution classification are the same or different types of classifiers. The same or different types of classifiers may be used for the same type of classification, such as different types of classifiers being used for different marginal space classification (e.g., the classifier for global motion is different than the classifier for surface location).

In one embodiment, the probabilistic model is formed from a plurality of probabilistic boosting tree classifiers. Separate training and resulting machine-trained classifiers are provided for each type of motion of interest. For each of these separate classifiers, separate probabilistic boosting tree classifiers are provided for each of the marginal space types. For example, the classifiers follow the marginal space learning protocol.

For application, the processor 12 calculates features for classification. The same or different features are used for classification in each stage. Using a machine-trained translation classifier, the features are used to rule out hypotheses, leaving a subset of remaining hypotheses.

The features are three-dimensional features. 3D data is used to calculate the features. The window function defining the data is a cube, but may have other volume shapes. The window is translated, rotated, and scaled as part of searching for an anatomy. The same or different sized windows are used for different anatomies.

Any features may be used. Different types of features may be used for the same classifier, or all of the features are of a same type for a given classifier. In one embodiment, Haar wavelet-like and/or steerable features are calculated. Haar wavelet-like features represent the difference between different portions of a region. Any number of features may be used, such as tens, hundreds, or thousands. The machine learning process may operate to determine a desired subset or set of features to be used for a given classification task. In one embodiment, the type of features used is gradient features. Other types of features may alternatively or additionally be used.

The processor 12 is configured to use the estimates. For example, a display is generated of the valve operation over time. As another example, a quantity is calculated and output on the image display, as a number or as part of a graph. Any quantity may be calculated, such as a quantity representing a characteristic of the valve motion. In one embodiment, the quantity is a function of information for two heart valves.

In one embodiment, the classifier is trained with measurement annotations, such as caliper positions. The detection of the anatomy provides the caliper positions as an output of the classifier. The measurement corresponding to the caliper position is performed, such as measuring a diameter or distance.

For simulation, the processor 12 creates the volumetric model. Using the anatomy model, the processor 12 adds characteristics. For example, chordae are added. As another example, fibers are added. In yet another example, a thickness or depth of the leaflets are added.

The parameters defining these added structures may be predetermined or user selectable. The processor 12 may receive an indication of one or more parameters. The indication may be by processing data. For example, different values of a parameter are attempted. The results are compared against the anatomy model or scan data. The value resulting in the greatest similarity is selected. The indication may be from a user, such as for manual selection.

The processor 12 applies the biomechanical model. The closure of the valve is simulated with the valve anatomy and the added characteristics of the volumetric model. The processor 12 applies emulation forces, such as blood pressure and chordae forces. Boundary conditions based on the locations of the anatomy in the anatomy model may be used to constrain the FEM solution. Collisions may be avoided or restricted. The volumetric model reaction to the forces is simulated. The simulation is of closure, but may be for other periods of the heart cycle.

The processor 12 simulates therapy. The placement of the clip may be simulated. The effect of clip placement on the otherwise static volumetric model may be simulated. The boundary conditions or anatomy locations are frozen with the valve in the open position for placement of the clip. This may indicate what occurs upon clip placement, such as simulating the clip as a spring displacing the leaflets closer together. The effect of clipping on the closure over time may be simulated.

The simulation may be based, at least in part, on the added characteristics of the volumetric model. These characteristics may be changed for repeated simulation. For example, the number, length, and/or other parameter of the chordae are used in simulation and may be changed. Once determined, the simulation for application of therapy is performed.

The processor 12 generates an image. The anatomy model, volumetric model, or simulation results (e.g., FEM based mesh locations) is used to generate an image. The patient-specific scan data may be used for imaging. The image provides a visualization of the closure of the valve with the valve clip or other therapy. The visualization may be of the valve prior to treatment or may be of the valve after treatment but not at closure.

The display 16 is a CRT, LCD, plasma, projector, printer, or other output device for showing an image. The display 16 displays an image of the detected anatomy, such as an image of a valve rendered from medical data and overlaid or highlighted based on the estimates of the valve position. The display 16 displays a sequence of renderings to generate a visualization of the valve motion through the sequence. The visualization for one time or a sequence may be generated during a same examination session as the scan. The detected anatomy may or may not be segmented, such as just displaying the valve. Alternatively or additionally, the displayed valve may be based on the volumetric model and biomechanical model application, so be different than the anatomy model alone. The images of the valve simulation may be a prediction of valve motion or closure when subjected to forces from treatment, such as clipping.

A value of a measurement may be displayed. The value may be displayed in a chart, graph, and/or on an image.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for valve treatment simulation from medical diagnostic imaging data, the method comprising:
   estimating, with a processor and a machine-learnt probabilistic model for anatomy detection, an anatomy model of a valve of a patient by inputting input features from the medical diagnostic imaging data of the patient into the machine-learnt probabilistic model;
   computing, with the processor, a volumetric model of the valve as open, the volumetric model being a function of the anatomy model and including chordae, the computing including extruding a leaflet atrial surface towards a ventricle and adding directional fibers in leaflets to the anatomical model;
   determining a length of the chordae for the patient;
   receiving locations for placement of a valve clip relative to the valve;
   simulating, with the processor, an effect of the valve clip on the volumetric model according to a biomechanical model;
   predicting, with the processor, the effect on the functioning of the valve, over a sequence of a heart cycle, after and caused by the placement of the valve clip at the locations on the valve, the predicting using the volumetric model and the length of the chordae with mitral annulus and papillary tip motions being constrained from the medical diagnostic imaging data and with limiting collisions of the leaflets; and
   displaying the effect of the placement of the valve clip at the locations on the valve.

2. The method of claim 1 wherein estimating comprises estimating from ultrasound data, computed tomography data, or dynaCT data representing a volumetric including the valve over time.

3. The method of claim 1 wherein estimating comprises estimating a location of anterior and posterior papillary tips, mitral annulus, and anterior and posterior leaflets.

4. The method of claim 1 wherein computing comprises computing the volumetric model from the anatomy model at an end-diastole phase of a heart cycle.

5. The method of claim 1 wherein computing comprises positioning the chordae in the anatomical model.

6. The method of claim 1 wherein simulating comprises simulating using a biomechanical model and a finite element solution.

7. The method of claim 1 wherein simulating comprises modeling leaflets as linear, transverse isotropic elastic tissues.

8. The method of claim 1 wherein simulating comprises modeling the chordae as piecewise tensile springs.

9. The method of claim 1 wherein simulating comprises applying a force from pressure.

10. The method of claim 1 further comprising:
    generating an image of the valve from the volumetric model with the valve as open;
    wherein receiving the location for placement of the valve clip relative to the valve comprises receiving a user selection relative to the image; and
    wherein simulating comprises simulating valve deformation due to the clip according to biomechanical model.

11. The method of claim 1 wherein simulating comprises simulating closure of the valve with the clip at the locations.

12. The method of claim 1 further comprising evaluating different chordae rest lengths in simulating closure of the volumetric model against the medical diagnostic imaging data; and
wherein determining the chordae length comprises selecting the optimal chordae rest lengths based on the evaluating.

13. The method of claim 1 wherein estimating, computing, and simulating are performed without user input of locations of anatomy represented in an image.

14. In a non-transitory computer readable storage medium having stored therein data representing instructions executable by a programmed processor for valve treatment simulation from medical diagnostic imaging data, the storage medium comprising instructions for:
scanning the imaging data of a patient;
modeling, with the processor and a machine-learnt probabilistic model for anatomy detection, closure of a valve based on scan data from the patient such that the closure is different for different patients, the modeling including chordae length for the patient, extruding a leaflet atrial surface towards a ventricle, adding directional fibers in leaflets to the anatomical model, constraining mitral annulus and papillary tip motions with the imaging data, and limiting collisions of the leaflets; and
simulating, with the processor, a sequence of operation including the closure of the valve from the modeling, the simulating including a force from after therapy.

15. The non-transitory computer readable storage medium of claim 14 wherein modeling comprises finite element modeling without user input of anatomy locations other than for locations of application of a clip in the therapy.

16. The non-transitory computer readable storage medium of claim 14 wherein modeling comprises adding force from chordae to the valve.

17. A system for valve treatment simulation from medical diagnostic imaging data, the system comprising:
an ultrasound scanner configured to scan a heart volume of a patient, the scan providing medical diagnostic ultrasound data representing a valve;
a processor configured to detect with a machine-learnt probabilistic model, as a function of application of the medical diagnostic imaging data to the machine-learnt probabilistic model, valve anatomy, the detection occurring during the scan, to simulate closure of the valve with the valve anatomy, to simulate placement of a valve clip on the simulation of the closure and to simulate a sequence of function of the valve, including closure of the valve, the sequence being for after placement of the valve clip, wherein the processor is configured to simulate the sequence with an extruded leaflet atrial surface towards a ventricle, added directional fibers in leaflets, mitral annulus and papillary tip motions being constrained with the imaging data, and collusions of the leaflets being limited; and
a display configured to generate a visualization of the closure with the valve clip.

18. The system of claim 17 wherein the processor is configured to simulate the closure as a function of a chordae and leaflet model.

* * * * *